United States Patent
Cazemier

(10) Patent No.: US 10,898,457 B2
(45) Date of Patent: *Jan. 26, 2021

(54) LACTYLATES FOR THE PREVENTION AND TREATMENT OF INFECTIONS CAUSED BY GRAM POSITIVE BACTERIA IN ANIMALS

(75) Inventor: Anne Cazemier, Leerdam (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/863,325

(22) PCT Filed: Jan. 23, 2009

(86) PCT No.: PCT/EP2009/050770
§ 371 (c)(1),
(2), (4) Date: Aug. 23, 2010

(87) PCT Pub. No.: WO2009/092787
PCT Pub. Date: Jul. 30, 2009

(65) Prior Publication Data
US 2010/0311832 A1    Dec. 9, 2010

(30) Foreign Application Priority Data
Jan. 25, 2008 (EP) ................. 08100911

(51) Int. Cl.
| | | |
|---|---|---|
| *A01N 37/00* | (2006.01) | |
| *A61K 31/215* | (2006.01) | |
| *A01N 37/12* | (2006.01) | |
| *A01N 37/44* | (2006.01) | |
| *A61K 31/24* | (2006.01) | |
| *A01N 25/00* | (2006.01) | |
| *A61K 31/23* | (2006.01) | |
| *A23K 20/105* | (2016.01) | |
| *A23K 50/10* | (2016.01) | |
| *A23K 50/75* | (2016.01) | |

(52) U.S. Cl.
CPC ............ *A61K 31/23* (2013.01); *A23K 20/105* (2016.05); *A23K 50/10* (2016.05); *A23K 50/75* (2016.05)

(58) Field of Classification Search
None
See application file for complete search history.

(56) References Cited

U.S. PATENT DOCUMENTS

| | | | | |
|---|---|---|---|---|
| 2,864,705 | A * | 12/1958 | Schulman ................ | A21D 2/16 426/612 |
| 5,911,981 | A * | 6/1999 | Dahms et al. ............ | 424/70.19 |
| 5,958,974 | A * | 9/1999 | Anderson ............ | A61K 31/225 514/547 |
| 2005/0053593 | A1 | 3/2005 | Wang et al. | |
| 2006/0051384 | A1 * | 3/2006 | Scholz et al. .................. | 424/405 |
| 2006/0062832 | A1 | 3/2006 | Lopes | |
| 2007/0010856 | A1 | 1/2007 | Cohen | |
| 2007/0085059 | A1 | 4/2007 | Mora-Gutierrez et al. | |

FOREIGN PATENT DOCUMENTS

| | | |
|---|---|---|
| CN | 101048064 A | 10/2007 |
| CN | 101053368 A | 10/2007 |
| EP | 1483975 A1 | 8/2004 |
| GB | 1115480 | 5/1968 |
| GB | 2163650 A | 3/1986 |
| WO | 96/37210 | 8/1996 |
| WO | 0106877 A1 | 2/2001 |
| WO | 2004037177 A2 | 5/2004 |
| WO | 2004107877 A1 | 12/2004 |

OTHER PUBLICATIONS

Gloxhuber et al. (Anionic Surfactants: Biochemistry, Toxicology, Dermatology, Second Edition, 1992).*
Tagg, John R., Adnan S. Dajani, and Lewis W. Wannamaker. "Bacteriocins of gram-positive bacteria." Bacteriological reviews 40.3 (1976): 722.*
Translation of Chinese Office Action, dated Aug. 3, 2011.
Abstract of CN101053368, Thomson Scientific, "Feed Additive Animal Comprise Lipase Emulsion Extract Subsidiary Material", Oct. 17, 2007.
International Search Report, dated Apr. 24, 2009.
Written Opinion.
Search Report issued for corresponding Chinese Patent Application No. 201310629600.X, dated Aug. 6, 2015.
Hofshagen et al. (Barley inclusion and avoparcin supplementation in broiler diets. 1. Effect on small intestinal bacterial flora and performance. Poult. Sci. 1992. 71:959-969).

(Continued)

*Primary Examiner* — Layla Soroush
(74) *Attorney, Agent, or Firm* — Westman, Champlin & Koehler, P.A.; Z. Peter Sawicki; Amanda M. Prose

(57) ABSTRACT

The present invention pertains to the use for preventing or treating intestinal infections caused by gram-positive bacteria in animals of an antibacterial compound selected from lactylate in accordance with formula 1, Formula 1 R2-COO—[—CH(CH$_3$)—COO]$_n$—R1 or a Na, K, Ca, Mg, Fe(II), Zn, NH$_4$, or Cu(II) salt thereof, a glycolylate of formula 2, Formula 2: R2-COO—[—CH2-COO]$_n$—R1 or a Na, K, Ca, Mg, Fe(II), Zn, NH$_4$, or Cu(II) salt thereof, a lactate ester of formula 3, Formula 3: HO—CH(CH$_3$)—COO—R2 and/or a glycolic acid ester of formula 4, Formula 4: HO—CH2-COO—R2 wherein R1 is selected from H, n stands for an integer with a value of 1-10, and R2 stands for a C1-C35 alkyl or alkenyl chain which may be branched or unbranched. The compound, which preferably is a lactylate or a Na, K, Ca, Mg, Fe(II), Zn, NH$_4$, or Cu(II) salt thereof, is particularly useful in the treatment or prevention of Clostridia. An animal nutrition composition and a method for preventing or treating infections are also claimed.

20 Claims, No Drawings

(56) References Cited

OTHER PUBLICATIONS

Hofacre et ai. 2003. Using competitive exclusion, mannan-oligosaccharide and other intestinal products to control necrotic enteritis. J. Appl. Poult. Res. 12:60-64.

Elwinger et al. (1992) "Factors affecting the incidence of necrotic enteritis, caecal carriage of Clostridium perfringens and bird performance in broiler chicks." Acta Vet. Scand.33:369-378.

Kaldhusdal et al. (2001) "Reduced incidence of Clostridium perfringens-associated lesions and improved performance in broiler chickens treated with normal intestinal bacteria from adult fowl." Avian Dis.45: 149-156.

Administrative Judgment of Beijing Intellectual Property Court of the People's Republic of China dated Oct. 21, 2020.

* cited by examiner

LACTYLATES FOR THE PREVENTION AND TREATMENT OF INFECTIONS CAUSED BY GRAM POSITIVE BACTERIA IN ANIMALS

CROSS-REFERENCE TO RELATED APPLICATION

This Application is a Section 371 National Stage Application of International Application No. PCT/EP2009/050770, filed Jan. 23, 2009 and published as WO 2009/092787 A1 on Jul. 30, 2009, the content of which is hereby incorporated by reference in its entirety.

BACKGROUND OF THE INVENTION

The present invention pertains to a method for preventing or treating intestinal infections caused by gram-positive bacteria in animals, to specified compositions for preventing or treating intestinal infections caused by gram-positive bacteria in animals, to the use of specified compositions for preventing or treating intestinal infections caused by gram-positive bacteria in animals, and to a nutrition composition for animals comprising a specific compound in an amount effective for preventing or treating intestinal infections caused by gram-positive bacteria in animals.

Gram-positive bacteria are stained dark blue or violet by gram staining, mainly due to a high amount of peptidoglycan in their cell wall. Among the gram positive bacteria are the pathogenic bacteria *Enterococcus, Clostridium, Listeria, Staphylococcus*, various *Bacillus* species, and *Streptococcus*. While some of these organism are mainly of concern as food contaminants, others can cause diseases in animals.

For example, Clostridia are responsible for causing a number of widely varying diseases of the intestine in animals. As it is a nearly ubiquitous bacteria readily found in soil, dust, faeces, and feed, it is extremely difficult to keep animals free from Clostridia.

*Clostridium*-related intestinal diseases may be quite severe. For example, Clostridia are involved in causing necrotic enteritis in chickens. In cattle, Clostridia-related enteritis can take the form of "sudden death syndrome", which, in practice can result in the in overnight deaths of a number of cattle. Also in other animals, Clostridia-related diseases may cause severe damage.

It is known to administer antibiotics to animals to protect them from intestinal infection. It is also known to include such antibiotics in animal nutrition. However, there is an increasing resistance against the use of antibiotics in animal feed, and nowadays many countries have legislation that prohibits the use of antibiotics in animal feed. Moreover, antibiotics have to be administered in very controlled amounts.

Accordingly, there is therefore a need for a non-antibiotic method and composition for animal feed that will help to treat or prevent intestinal infections caused by gram-positive bacteria in animals, in particular in mammals, including ruminants (e.g. cattle, sheep, goat, deer) and monogastrics (e.g. swine, horses, rabbits); in birds (e.g. poultry, turkey, pheasant, quail); in fish, including marine fish (e.g. salmon halibut, tuna), fresh water fish (e.g. trout, carp, tilapia); molluscs (e.g. oyster, mussels, clam, snail) and crustacean (e.g. crab, lobster, shrimp). The present invention may also find application in humans, and in fur animals such as mink, ermine, sabre, and foxes.

Further, it may be desirable to suppress specific Gram-positive bacteria in the intestine with a view to increasing the growth of animals. It is believed that this may be of interest for *Lactobacillus* spp. The present invention is also of interest for this application.

SUMMARY OF THE INVENTION

The present invention provides a method and composition for animal feed for treating or preventing intestinal infections caused by gram-positive bacteria in animals. In accordance with the present invention, use is made of an antibacterial compound selected from lactylate in accordance with formula 1,

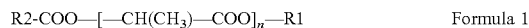

or a Na, K, Ca, Mg, Fe(II), Zn, $NH_4$, or Cu(II) salt thereof, a glycolylate of formula 2,

or a Na, K, Ca, Mg, Fe(II), Zn, $NH_4$, or Cu(II) salt thereof a lactate ester of formula 3,

and/or a glycolic acid ester of formula 4,

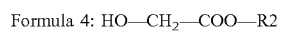

wherein in the above formulas R1 is selected from H, n stands for an integer with a value of 1-10, and R2 stands for a C1-C35 alkyl or alkenyl chain which may be branched or unbranched for the prevention or treatment of intestinal infections caused by gram-positive bacteria.

DETAILED DESCRIPTION OF ILLUSTRATIVE EMBODIMENTS

The present invention pertains to the prevention or treatment of intestinal infections by gram-positive bacteria in animals. The invention is particularly attractive for use against intestinal infections with anaerobic or facultative anaerobic bacteria, even more in particular anaerobic bacteria. Within the group of anaerobic bacteria, it is particularly desirable to have a method for the prevention or treatment of intestinal infections by spore-forming bacteria, as these organism tend to be difficult to control. The invention is of particular interest in the prevention and treatment of intestinal infections by Clostridia.

In one embodiment, the present invention pertains to the prevention or treatment of intestinal infections caused by *Clostridium*, in particular by *Clostridium perfringens* in poultry, in particular in chicken.

In another embodiment the present invention pertains to the prevention or treatment of intestinal infections caused by *Clostridium*, in particular by one or more of *Clostridium tetanii, novyi* (type B) *septicum, chauvii, sordelii, hemolyticum, difficile, botulinum*, in cattle.

In a further embodiment the present invention pertains to the reduction of intestinal growth of *Lactobacillus* spp.

It is noted that WO 2004/107877 describes an antimicrobial composition comprising a mixture of lactic acid or a derivative thereof and an inorganic acid. The composition is described as antimicrobial in general. The use against *Salmonella* and *Escherichia Coli* is specified. While lactylates are mentioned as possible lactic acid derivatives, their use is not further elucidated. There is nothing in this reference that teaches or suggests the particular efficacy that the use of lactylates has been found to show against gram-positive bacteria in animals.

It is further noted that GB115480 describes the use of acylated alpha-hydroxy carboxylic acids against bacteria and fungi, for instance moulds, mildews, and yeasts. It is indicated that the compound can be used for consumption by or application to humans or other animals, but this is never elucidated. There is nothing in this reference that teaches or suggests the particular efficacy that the use of lactylates has been found to show against gram-positive bacteria.

In the present invention, use may be made of an antibacterial compound selected from one or more of a lactylate in accordance with formula 1, or a Na, K, Ca, Mg, Fe(II), Zn, $NH_4$, or Cu(II) salt thereof, a glycolylate of formula 2, or a Na, K, Ca, Mg, Fe(II), Zn, $NH_4$, or Cu(II) salt thereof, a lactate ester of formula 3, and/or a glycolic acid ester of formula 4.

The use of a lactylate of formula 1 or a salt thereof has been found to be preferred.

In a preferred embodiment of the present invention, R2 is an alkyl or alkenyl chain with 6-20 carbon atoms. More in particular, R2 is an alkyl or alkenyl chain with 6-18 carbon atoms. In this embodiment, suitable substituents include groups with 6 carbon atoms (capronic), 8 carbon atoms (caprylic) 10 carbon atoms (capric acid), 12 carbon atoms (lauryl), 14 carbon atoms (myristyl), 16 carbon atoms (cetyl, palmityl), 18 carbon atoms (stearyl). Mixtures of two or more compounds may also be used. Where a salt is used, the use of a Na, K, Ca, or Mg salt may be particularly preferred.

The value for n is preferably in the range of 1-5. More in particular n has a value of 1, 2, or 3.

The use of lauroyl lactylate, myristolyl lactylate, and their sodium salts is particularly preferred. In one embodiment, a mixture is used comprising 5-95 wt. % of lauroyl lactylate and 95-5 wt. % of myristoyl lactylate, or the sodium salt(s) of these compounds are used, more in particular, a mixture is used comprising 25-75 wt. %, more in particular 40-wt. % of lauroyl lactylate, and 75-25 wt. %, more in particular 40-60 wt. % of myristoyl lactylate, or the sodium salt(s) of these compounds.

In one embodiment of the present invention, the antibacterial compound, in particular the lactylates or salts thereof, are used in combination with one or more coccidostatic components. This is of particular interest in poultry during the immunosuppression period, which is the period in a chick's lifetime where the immune system which protects the animal in the egg has deteriorated but the immune system of the animal itself has not been completely developed. For chickens this is between day 10 and 20 of the animals lifetime.

This is of particular interest increase the resistance of the chicken to intestinal *Clostridium* infections. More in particular, in chicken it is believed that the necrotic enteritis caused by *Clostridium* is often preceded by an infection with *Eimeria*. The *Eimeria* is believed to damage the wall of the intestines, which makes it less resistant to an infection with *Clostridium*. The use of a combination of lactylate with one or more coccidostatic components will therefore provide an increased resistance of the chicken against necrotic enteritis.

Suitable coccidostatic components are known in the art, as are the amounts in which they should be provided. Suitable components include maduramycine, diclrzil, narasin, nicarbazine, monensin, robenidine, lasalocid, halofuginon, narasin, salinomycine, decoquinate, and semduramycine.

The composition may be administered to animals as a component of a conventional animal feed composition. In the context of this invention the term "animal nutrition" includes solid feed and liquid feed, such as drinking water. Thus, the composition may be administered to an animal as a solid or liquid component of a conventional animal feed composition or in their drinking water.

The composition may also be administered to the animal in a separate step, independent from the provision of a conventional animal feed composition.

In one embodiment of the invention, the antibacterial compound, in particular the lactylate or salt thereof, is attached to a support. This provides a convenient way to obtain the antimicrobial composition in solid powdered form. Suitable supports are selected from vegetable fiber material, vegetable carbohydrates such as cellulose, and mineral supports such as silica, starch, gypsum, and lime.

In another embodiment, the antimicrobial compound is added in a mixture with a vegetable oil, e.g., a corn oil, soybean oil, or olive oil.

The anti-microbial compound may also be in the form of a tablet or other shaped body known for provision of pharmaceutical components to animals.

The amount of antimicrobial compound, in particular lactylate, administered to the animal is such that it is effective to treat or prevent intestinal infections caused by gram-positive bacteria in the animal to which the compound is administered. Such an amount is suitably in the range from 0.0001-5% based on the total weight of each feed fed to the animal. In a preferred embodiment, the amount may be in the range of 0.001 to 2%, based on the total weight of each feed fed to the animal. It has been found that as compared to the use of lactic acid as described in WO 2004/107877 it may be possible to use lower concentrations of the effective component. While in the Examples of WO 2004/107877 1.2 wt. % of lactic acid is used, the use of, for example, lactylates in accordance with the present invention allows the use of a reduced amount of active component. Accordingly, in one embodiment of the present invention the amount may be in the range of 0.001 to 1 wt. %, more in particular 0.001 to 0.5 wt. %, based on the total weight of each feed fed to the animal. It is within the scope of the skilled person to determine the amount necessary.

If so desired, the amount may be higher than required for the compound to be effective to treat or prevent infections caused by gram-positive bacteria Clostridia-related enteritis in the animal. This may be the case if the compound also acts to promote growth, improve feed to gain ratio, and/or improves digestibility of amino acids administered in animal feeds.

As mentioned above, the antibacterial compound may be administered to animals as a component of a conventional animal feed composition. A conventional animal feed composition may comprise wheat, starch, meat and bone meal, maize, sunflower meal, corn, cereals, barley, soybean meal, tapioca, citrus pulp, legumes, beet pulp, etcetera. In accordance with the present invention the provision of antibacterial compounds to the animal to treat or prevent intestinal infections with Gram-positive bacteria will in general not be combined with the provision of antibiotics.

In WO 2004/107877 lactic acid or a lactic acid derivative is used in combination with an inorganic acid selected from nitrogen, sulphur, and phosphorus-containing acids. It is indicated that the inorganic acid is believed to lower the pH in the chymus during total passage in the animal, thereby increasing the presence of non-dissociated lactic acid, which disrupts the outer membrane of the pathogens.

In contrast, the present invention does not rely on the presence of non-dissociated lactic acid. Therefore, the present invention does not require the presence of an inorganic acid to lower the pH in the chymus.

Accordingly, the present invention also pertains to the use of antibacterial compounds as described above, in particular lactylates according to formula 1, in the prevention or treatment of intestinal infections caused by gram-positive bacteria, wherein such use is not accompanied by the use of an inorganic acid selected from nitrogen, sulphur, and phosphorus-containing acids for increasing the presence of non-dissociated lactic acid.

The invention is further illustrated by the following examples, which show the inventive merits of this invention, without the invention being limited thereto or thereby.

Example 1

Efficacy of a Mixture of Sodium Lauroyl Lactylate And Sodium Myristoyl Lactylate Against Necrotic Enteritis in Chicken The efficacy of a mixture of sodium lauroyl lactylate and sodium myristoyl lactylate against necrotic enteritis in chicken has been evaluated by Schothorst Feed Research in an experimental *C. perfringens* infection model which they have developed in which a coccidiosis infection is used as a pre-trigger for *C. perfringens* to colonise the small intestine and cause necrotic enteritis. A coccidiosis infection is initiated by a pathogenic *Eimeria maxima* and, on the peak of the coccidiosis infection, birds are inoculated with a *C. perfringens* strain that proved to be pathogenic to broiler chickens. A coccidiosis infection caused by *E. maxima* (resulting in lesions in the middle segment of the small intestine) followed by a *Clostridium* infection results in a highly reproducible model and an easy and accurate way of scoring for necrotic enteritis lesions, because lesions of *E. maxima* and *Clostridium* are easy to distinct while lesions of both pathogens do not occur in the same intestinal segment. The experiments are performed in cooperation with the Animal Health Service (GD).

The experiment consisted of one treatment and two control treatments. All treatments consisted of six replicate cages with 19 broilers per cage. The treatments are given in Table 1.

TABLE 1

Description of the treatments and diet codes

| Trt. | Day 9 Inoculum: | Day 14, 15 and 16 | Supplementation of additive | Remark |
|---|---|---|---|---|
| 1. | Saline | Liver broth | — | Control |
| 2. | *Eimeria maxima* | *C. perfringens*[2)] | — | Control/ Experimental |
| 3. | *Eimeria maxima* | *C. perfringens* | test mixture (0.3% mixture of 50 wt. % sodium lauroyl lactylate and 50 wt. % myristoyl lactylate) | Experimental |

[1)] 10,000 of sporulated oocysts of *Eimeria maxima* in 1 ml
[2)] 1 × 10$^8$ cfu *C. perfringens* in 1 ml Animals, Management and Procedures One day-old male Ross 308 broiler chickens were supplied by Probroed & Sloot B. V., the Netherlands. At day 0, broilers arrived at the laboratory facilities of the Animal Health Service (Deventer, the Netherlands) and were housed in digestibility cages after individual weighing. Based on a weight-class system 19 birds were allotted to 30 Schothorst litter floor digestibility cages, resulting in a similar mean weight per cage. Broilers were housed in these cages until the end of the experiment at day 20. At day 9, if no mortality occurred, the number of chickens was standardised to 17 and bird weight was measured again. First, birds with obvious visual aberrations were removed and second, birds were removed at random to decrease the number to 17. Lighting and temperature schedule throughout the experimental period was as follows, 22 hours of light followed by 2 hours darkness in the first period from day 0 to 9 followed by 18 hours of light and 6 hours darkness throughout the rest of the experiment. The ambient temperature was gradually decreased from 32° C. at the start to 25° C. at the end of the experiment.

Feed was supplied for ad libitum intake from day 0 onwards with exception of the 5 hours prior to inoculations (days 9, 14, 15 and 16) and sections (days 15, 16 and day 20). Water was available for ad libitum intake throughout the experiment.

Feed Composition

The broilers were supplied a wheat/soybean meal-based starter diet from day of arrival until day 9. From day 9 onwards, a wheat/barley-based grower diet was fed until the end of the experiment (day 20). Grower feeds were fed as meals because of the necessity of homogenously mixing in the test products after feed production. Diets did not contain any coccidiostats or antimicrobial feed additives other than the test product. The nutrient composition of the experimental diets was according to Dutch standards to meet nutrient requirements of broilers (CVE, 2006).

Inoculum

At day 9, broilers were inoculated with either 1 ml saline or *E. maxima* (10.000 sporulated oocysts/chicken in 1 ml) after a 5 hours feed withdrawal period. From day 14 onwards, broilers were either inoculated with 1 ml liver broth (DIFCO) or *C. perfringens* once per day persisting three days after a 5 hours feed withdrawal. A detailed overview of the different treatments is presented in Table 1.

The pathogenic *C. perfringens* strain was obtained from the Animal Health Service in Deventer, the Netherlands (approx. 10$^8$ cfu in 1 ml). The strain was grown on an agar of sheep blood and the culture is typed by CIDC (Central Institute of Animal Disease Control in Lelystad) as *C. perfringens* producing type α and β2 toxins. Each day a freshly prepared inoculum was used.

Lesion Scoring

*Clostridium perfringens*: Gross and microscopic lesions generally occur in the small intestine, particular in the proximal site. The following scoring method was used:

0: no lesions
1:1 to 5 small lesions (spots of less than 1 mm diameter)
2: more than 5 small lesions (spots of less than 1 mm diameter) or 1 to 5 larger lesions (spots of 1 to 2 mm diameter)
3: more than 5 larger lesions (1 to 2 mm diameter) or erosive zones
4: dead birds with positive necrotic enteritis diagnoses post mortem All birds were scored "blind", i.e. the person scoring the birds for lesions did not have knowledge of the birds treatment.

Measurements

During the experiment the following parameters were measured:

Individual body weight at day of arrival and means per cage at day 9 and day 20 of the experiment
Body weight of the birds prior to necropsy Feed intake per cage in the periods from day 0 to 9 and daily feed intake from 9-20 days of age Coccidiosis lesions and necrotic enteritis lesions in the small intestinal mucosa of 24 birds per treatment at day 15, day 16 and day 20 of the experiment (total of 72 birds per treatment).

Mortality per cage from 0 to 20 days of age.

Daily records were kept of all routine study activities, health disorders and of mortality (with its most probable cause).

Statistical Analyses

Raw data were analysed for outliers. Significant outliers were excluded from the statistical analysis. The incidence of NE-lesions (% of affected birds) was analysed by Fisher Exact Test, whereas the severity of lesions and daily feed intake measurements were analysed by analysis of variance (ANOVA) using Genstat statistical software. Treatment means were compared by the least significant difference (LSD). $P \leq 0.05$ was considered to be statistically significant, whereas $0.05 < P \leq 10.10$ was considered to be a near-significant trend.

Results and Discussion

Incidence and Severity of Lesions

Lesion Scoring at Day 15 (1 Day Post Infection)

In Table 2, the percentage of positive scored birds (birds with NE lesions) is given as well as the mean lesion score of all positive scored birds. Because the mean lesion score of all examined birds, affected as well as unaffected, gives a more representative picture for the population, statistical analyses have been performed over these results (see the fifth column of Table 2). The severity of lesions in both positive and negative scored birds is indicated on a scale of 0 to 4 (see section "lesion scoring").

TABLE 2

Birds observed with NE (%) and the mean severity of lesions scored at day 15 (1 day p.i.).

| Group | Treatment | Dosage | Positive birds (%) | Lesion severity | Lesion severity pos. birds) [1] |
|---|---|---|---|---|---|
| 1 | Negative control | — | 0 [a] | 0.0 [a] | 0.0 |
| 2 | Positive control | — | 16 [a b] | 0.5 [b] | 3.0 |
| 3 | Test mixture | 0.3% | 17 [a b] | 0.4 [b] | 2.5 |

[a, b] Values with no common superscript in a column differ significantly ($P \leq 0.05$).
[1] Lesions severity of NE-positive scored birds A significant treatment effect was observed on the NE incidence. As expected, the lowest incidence was observed in the uninfected control treatment but results were comparable to the results of the treatments supplemented with the test mixture and unsupplemented infected control.

Based on the ANOVA it was concluded that there was a significant treatment effect on the severity of necrotic lesions on day 15 (P<0.001). On lesion severity it was evident that lesions were more severe in the infected treatments, unsupplemented as well as supplemented, than the uninfected control treatment for there were no positive score birds in the latter. Among the infected treatments no statistical differences were observed.

Lesion Scoring at Day 16 (2 Days Post Infection)

In Table 3, the percentage of positive-scored birds and the mean lesion score of birds is given for day 16.

TABLE 3

Birds observed with NE (%) and the mean severity of lesions scored in all necropsied birds at day 16 (2 days p.i.).

| Group | Treatment | Dosage | Positive birds (%) | Lesion severity | Lesion severity pos birds) [1] |
|---|---|---|---|---|---|
| 1 | Negative control | — | 0 [a] | 0.0 [a] | 0.0 |
| 2 | Positive control | — | 68 [b] | 2.1 [c] | 3.2 |
| 3 | Test mixture | 0.3% | 41 [b] | 1.1 [b] | 2.7 |

[a, b] Values with no common superscript in a column differ significantly ($P \leq 0.05$).

Comparing the results of NE incidence and lesion severity on day 16 to the results of day 15, it is clear that the severity of infection was higher 2 days post infection. Although again a significant treatment effect was observed on the NE incidence, it is evident that this is due to the difference between the uninfected control treatment and infected treatments, which is as expected, whereas among infected treatments there was no significant difference observed.

A sharp distinction can be drawn on lesion severity days post infection. The treatment supplemented with the test mixture resulted in a clear reduction in lesion severity compared to the infected unsupplemented control, although mean lesion scores were still higher than the uninfected control.

Lesion Scoring at Day 20 (6 Days Post Infection)

At day 20 no significant differences was observed between treatments. All treatments recovered from NE, at least based on macroscopical evaluation, with 0% incidence and obviously 0.0 for lesion severity.

Mortality

Mortality is one of the parameters to measure the severity of an infection with *Clostridium* in a flock. In this experiment the mortality was compared among treatments. Mortality was 14.6% in the infected control treatment (treatment 2) and 0% in the uninfected control. Supplementation of the test mixture resulted in a reduction in mortality (5.1%).

Production Parameters

Besides lesions scoring, production parameters like body weight and daily feed intake were measured during the trial period.

Body weight of one day-old broilers was in all treatments approx. 47 grams. Because treatments from day 0 to 9 were similar, no differences in body weight gain and feed intake were observed in this period.

In the infection period from day 9 to 20 both production parameters were significantly affected by the individual treatments. Body weight gain was highest in the uninfected control, as expected, while broilers in the infected unsupplemented treatments showed the lowest body weight gain. This resulted in a 30% lower final weight at day (523 g versus 749 g). The infected supplemented treatment resulted in a significantly higher feed intake and body weight gain compared to the infected unsupplemented control.

Reduction in production performance could be reduced with 10% showing a loss in final weight of approx. 20% when compared to the uninfected control group (approx 583 g versus 749 g). It was concluded that the test mixture significantly increased production performance during a subclinial *Clostridium* infection.

Example 2

In Vitro Tests of Lactylates Against *Clostridium*

Liquid cultures of *Clostridium perfringens* ATCC 13124 were grown in screw-capped tubes (100×16 mm) containing 10 ml brain heart infusion broth (Oxoid CM225, Basingstoke, United Kingdom) for 24 hours at 30° C. Brain heart infusion broth was prepared with varying amounts of lactylates. The pH of the media was adjusted to 6.0 with 9 M sulphuric acid using a Handylab pH 12 pH meter equipped with a Blueline 16 pH (micro) probe (no. 285129163). All media were sterilised by filtration using 0.45 μm cellulose acetate filters (Minisart syringefilter, sterile and non-pyrogenic, no. 16555, Sartorius, Göttingen, Germany) (9). 300 μl of each medium was transferred to a panel of a sterile Bioscreen honeycombe 100 well plate (Thermo electron Oy, Vantaa, Finland). Completed well plates were stored at −30° C. until further use.

Well plates were inoculated with 3 μl culture using a sterile Hamilton repeating dispenser (Hamilton, Bonaduz, Switserland). The growth rate of the test organisms was determined at 30° C. with the Bioscreen C culture system (Oy Growth Curves AB Ltd, Helsinki, Finland). In order to assure low oxygen conditions the Bioscreen was placed inside an anaerobic cabinet equipped with a type M-12 oxygen sensor (In Vivo$_2$ 400 hypoxia workstation, Biotrace International Plc, Bridgend, United Kingdom). The oxygen tension was regulated at 0% oxygen using a Ruskinn gas mixer module (Biotrace International Plc). The Bioscreen C kinetically measures the development of turbidity by vertical photometry in up to 200 wells simultaneously. The optical density of the cultures was automatically measured at fixed time intervals at 420-580 nm using a wide band filter.

Table 4 shows the MIC values for the various lactylates tested for *Clostridium perfringens* ATCC 13124 in brain heart infusion broth. In the parentheses the number of repeats is given. MIC stands for the Minimal Inhibitory Concentration, which is the lowest concentration where the increase in absorbance of a culture did not exceed the threshold value, which was defined as the average increase in absorbance value of the blanks plus three times the standard deviation.

It appears that even at very low concentration lactylates are capable of suppressing the growth of *Clostridium perfringens*.

TABLE 4

MIC values of different lactylates

| Lactylates | MIC values (%) |
|---|---|
| C8 lactylate | 0.05% (2×) |
| C10 lactylate | 0.04% (2×) |
| C12 lactylate | 0.002% (2×) |
| C14 lactylate | 0.001% (2×) |
| C16 lactylate | 0.002% (2×) |
| C18:1 lactylate | 0.02% (2×) |
| Mixture of 1:1 C10/C12 lactylate) | 0.002% (3×) |
| Mixture of 1:1 C12/C14 lactylate | 0.001% (3×) |

Example 3

Dose-Response Studies and Prevention Studies of a Mixture of Sodium Lauroyl Lactylate and Sodium Myristoyl Lactylate Against Necrotic Enteritis in Chicken Analogous to Example 1, the influence of the dose of the compound was studied. Further, the use of the mixture on chicken which were not previously infected with *Emeria* and *Clostridium* was studied.

The treatments performed are summarised in Table 5:

TABLE 5

Description of the treatments

| Trt. | Description |
|---|---|
| 1. | Uninfected |
| 2. | Uninfected + 0.3% test mixture |
| 3. | Infected [1)] |
| 4. | Infected + 0.6% test mixture |
| 5. | Infected + 0.3% test mixture |
| 6. | Infected + 0.3% test mixture (silica) |
| 7. | Infected + 0.15% test mixture |
| 8. | Infected + 0.075% test mixture |
| 9. | Infected + 0.038% test mixture |
| 10. | Infected + 0.019% test mixture |
| 11. | Infected + 0.010% test mixture |
| 12. | Infected + 0.005% test mixture |

The test mixture was made up of 50 wt. % of sodium lauroyl lactylate and 50 wt. % of myristoyl lactylate.

The results may be summarised as follows.

In this experiment a subsequent infection with *E. maxima* and *C. perfringens* resulted in an incidence of necrotic enteritis of 56% and an average lesion score of 1.6 during the first two days post infection. Supplementing bird diets with test mixture reduced the number of infected birds and a dose response effect was observed, showing the highest efficacy in the 0.6% and 0.3% treatments. Lesion severity was significantly reduced due to test mixture supplementation and the dose response effect was also strongly present on this parameter. Lesions were less severe in the treatments with the highest doses of test mixture. The test mixture supplemented in a pure form resulted in a somewhat better response than the test mixture supplied via a silica carrier. Supplementation of test mixture with 0.6% resulted in a significant reduction in mortality (4.6%) and was not significantly higher than the not infected control treatment. Results with 0.3% test mixture supported the results observed in the lesion scoring.

With regard to production performance an effect was observed when comparing healthy birds with or without test mixture supplementation with each other. The provision of test mixture tended to increase body weight in the starter phase and grower phase. Supplementing infected birds with higher doses of test mixture resulted in the birds having a similar final weight (day 37) as birds that were not infected at all.

It can be concluded that the test mixture, especially in a dose of 0.3 wt. % or higher is effective in preventing necrotic enteritis development in broiler by showing a lower incidence and lesions that were less severe.

Although the present invention has been described with reference to preferred embodiments, workers skilled in the art will recognize that changes may be made in form and detail without departing from the spirit and scope of the invention.

The invention claimed is:

1. A method for treating intestinal infections caused by gram-positive bacteria in animals, the method comprising feeding the animal with an effective amount of an antimicrobial compound selected from myristoyl lactylate, and the Na, K, Ca, or Mg salts thereof.

2. The method according to claim 1, wherein the animal is fed mixture comprising lauroyl lactylate and myristoyl lactylate or the sodium salts thereof.

3. The method according to claim 1, wherein the animal is fed a mixture comprising 5-95 wt. % of lauroyl lactylate and 95-5 wt.-% of myristoyl lactylate, or the sodium salts of these compounds.

4. The method according to claim 1, wherein the animal is selected from cattle or poultry.

5. The method according to claim 1, wherein the gram-positive bacteria is of the genus Clostridia.

6. The method according to claim 1, wherein the antibacterial compound is fed in combination with a coccidostatic.

7. The method according to claim 1, wherein the antibacterial compound is present on a support.

8. The method according to claim 1, wherein the antibacterial compound is present in an amount of 0.001 wt. % to 1.0 wt. % or 0.001 wt. % to 0.5 wt. %, based on the total weight of each feed fed to the animal.

9. The method according to claim 1, wherein the antibacterial compound is fed in the absence of an inorganic acid selected from nitrogen, sulphur, and phosphorus-containing acids for increasing the presence of non-dissociated lactic acid.

10. A method for suppressing the growth of pathogenic gram-positive bacteria in the intestines of animals, the method comprising feeding the animal with an effective amount of an antimicrobial compound selected from; myristoyl lactylate, the sodium salts thereof, and mixtures thereof.

11. A method for treating intestinal infections caused by gram-positive bacteria in animals, the method comprising feeding the animal an animal feed comprising an effective amount of an antibacterial compound, the antibacterial compound comprising myristoyl lactylate or the Na, K, Ca, or Mg salts thereof and the antibacterial compound being provided in an amount ranging from 0.001 wt. % to 0.5 wt. % based on the total weight of the animal feed fed to the animal.

12. The method according to claim 11, wherein the animal feed comprises a mixture comprising lauroyl lactylate and myristoyl lactylate or the sodium salts of these compounds.

13. The method according to claim 11, wherein the animal feed comprises a mixture comprising 5-95 wt. % of lauroyl lactylate and 95-5 wt.-% of myristoyl lactylate, or the sodium salts of these compounds.

14. The method according to claim 11, wherein the animal is selected from cattle or poultry.

15. The method according to claim 11, wherein the gram-positive bacteria is of the genus Clostridia.

16. The method according to claim 11, wherein the animal feed further comprises a coccidostatic.

17. The method according to claim 1, wherein the animal is fed a mixture comprising 25-75 wt. % of lauroyl lactylate and 75-25 wt. % of myristoyl lactylate, or the sodium salts of these compounds.

18. The method according to claim 1, wherein the animal is fed a mixture comprising 40-60 wt. % of lauroyl lactylate and 60-40 wt. % of myristoyl lactylate, or the sodium salts of these compounds.

19. The method according to claim 11, wherein the animal feed comprises a mixture comprising 25-75 wt. % of lauroyl lactylate and 75-25 wt. % of myristoyl lactylate, or the sodium salts of these compounds.

20. The method according to claim 11, wherein the animal feed comprises a mixture comprising 40-60 wt. % of lauroyl lactylate and 60-40 wt. % of myristoyl lactylate, or the sodium salts of these compounds.

* * * * *